(12) United States Patent
Leinweber et al.

(10) Patent No.: US 7,208,118 B2
(45) Date of Patent: Apr. 24, 2007

(54) PROCESS FOR THE SOLVENT-FREE PREPARATION OF ETHERCARBOXYLIC ACIDS HAVING A LOW RESIDUAL SALT CONTENT

(75) Inventors: Dirk Leinweber, Schwalbach (DE); Uwe Dahlmann, Heidelberg (DE); Rainer Kupfer, Hattersheim (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 162 days.

(21) Appl. No.: 11/072,033

(22) Filed: Mar. 4, 2005

(65) Prior Publication Data
US 2005/0197261 A1 Sep. 8, 2005

(30) Foreign Application Priority Data
Mar. 4, 2004 (DE) .................. 10 2004 010 505

(51) Int. Cl.
*C23F 11/04* (2006.01)
*C07C 59/125* (2006.01)

(52) U.S. Cl. ....................................... 422/17; 562/587

(58) Field of Classification Search ............... None
See application file for complete search history.

(56) References Cited

U.S. PATENT DOCUMENTS

| 4,625,057 | A | 11/1986 | Springmann et al. |
| 5,840,973 | A | 11/1998 | Yasukohchi et al. |
| 6,326,514 | B1 | 12/2001 | Klug et al. |
| 2003/0194388 | A1 | 10/2003 | Dahlmann et al. |

FOREIGN PATENT DOCUMENTS

DE 39 24201 1/1991
EP 1061064 12/2000

OTHER PUBLICATIONS

English Abstract of DE 39 24201, published Jan. 24, 1991.
EP Search Report for Application EP05003714.2-2108PCT, Dated Jul. 27, 2005.

Primary Examiner—Paul A. Zucker
(74) Attorney, Agent, or Firm—Richard P. Silverman

(57) ABSTRACT

The invention provides a process for preparing compounds of the formula (1)

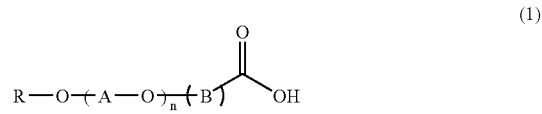

(1)

where A is $C_2$- to $C_4$-alkylene, B is $C_1$- to $C_4$-alkylene, n is a number from 1 to 100, and R is $C_1$- to $C_{30}$-alkyl, $C_2$- to $C_{30}$-alkenyl, or $C_6$— to $C_{30}$-aryl, by a) alkylating a basic mixture of oxoalkylated alcohols of the formula R—O-(-A-O—)$_n$—H and alkoxides thereof with a $C_2$- to $C_5$-chlorocarboxylic acid in the absence of a solvent, b) converting the thus obtained ethercarboxylic acid salt to the free ethercarboxylic acid by adding an acid, the pH being adjusted to 3 or less, c) freeing the thus obtained ethercarboxylic acid, without washing, of water present down to a residual water content of <0.30% by distillation under reduced pressure, and d) removing the precipitated metal salts by filtration, so that the resulting product has a residual salt content of <0.2%.

10 Claims, No Drawings

PROCESS FOR THE SOLVENT-FREE PREPARATION OF ETHERCARBOXYLIC ACIDS HAVING A LOW RESIDUAL SALT CONTENT

The present invention relates to a process for the solvent-free preparation of ethercarboxylic acids having a low residual salt content, and the use thereof as metalworking assistants, in cosmetics formulations and as detergents in cleaning compositions.

Ethercarboxylic acids, i.e. organic carboxylic acids which, in addition to the carboxyl function, bear one or more ether bridges, or the alkali metal or amine salts thereof, are known to be mild detergents having a high lime soap dispersion capacity. They find use both in laundry detergent and cosmetics formulations, and in industrial applications, for example metalworking fluids, and cooling lubricants.

According to the prior art, ethercarboxylic acids (ECA) are prepared either by alkylating alcohol or fatty alcohol oxyethylates or oxypropylates with chloroacetic acid derivatives (Williamson ether synthesis/carboxyalkylation) or from the same starting materials by oxidation with various reagents (atmospheric oxygen, hypochlorite, chlorite) under catalysis with various catalysts. On the basis of the cost-benefit analysis in particular, the Williamson ether synthesis constitutes the industrially most common process for the preparation of ECA, but products prepared by this process still have serious shortcomings in relation to the ease of handling for the user, for example solubility behavior, state of matter at low temperatures and in particular the rather high residual salt content which can lead to increased corrosion.

These shortcomings can substantially be attributed to process-related secondary constituents. For instance, despite use of excesses of the appropriate chloroacetic acid derivative, only conversions of approx. 70–85% are achieved, so that residual amounts of oxyethylate and the parent fatty alcohol of the oxyethylate remain in the end product. In addition, the excess of the chloroacetic acid derivative to be used results in subsequent products, for example glycolic acid, diglycolic acid and derivatives thereof, which are a substantial cause of the aging of the products and can in some cases cause problems in the solubility behavior.

A further serious disadvantage of the Williamson synthesis consists in the high contamination of the reaction products by sodium chloride (content approx. 1%) which constitutes a substantial cause of pitting corrosion in aqueous solutions. The sodium chloride content can be reduced by washing processes with saturated aqueous solutions of other metal salts. However, this only substitutes the sodium chloride content for the content of the corresponding metal salt of the washing phase. Thus, it is not possible to prepare a reaction product which has reduced corrosive properties.

DE-A-199 28 128 discloses a process for preparing ethercarboxylic acids having a low residual alcohol content, by reacting fatty alcohols initially with alkylene oxides using noncatalytic amounts of alkali metal catalyst (NaOH, KOH, alkoxides above 5 mol %), and subsequently converting the resulting, strongly alkaline reaction mixtures which consist of a mixture of oxyethylated alcohols and alkoxides of various polyalkylene glycol ethers in a classical Williamson synthesis with sodium chloroacetate to the corresponding ethercarboxylic acid. Although this process reduces the residual content of fatty alcohol in the ethercarboxylic acid without special catalysts, the high residual content of the product phase is not reduced.

EP-A-0 897 906 describes a process for preparing polyoxyalkylene carboxylic acids. In this process, the ethercarboxylic acids described are prepared by the industrially customary process. However, firstly, the carboxyalkylation step is carried out with the aid of a solvent, and, secondly, the organic product phase is purified using a washing process with an aqueous solution of a metal salt. This is intended to provide a highly pure ethercarboxylic acid. Both the use of a solvent and of the washing process described is economically and ecologically disadvantageous. In addition, the washing process described leads merely to a substitution of the sodium chloride stemming from the carboxyalkylation step by another salt. Therefore, the organic crude product cannot be freed of metal salts with such a washing process. The ethercarboxylic acids described are said to be highly pure, but no residual salt contents are disclosed, nor are any decision criteria specified in order to detect a low residual salt content.

It is therefore an object of the invention to develop an economically and ecologically advantageous process for preparing ethercarboxylic acids, which is notable for a particularly low residual salt content.

It has been found that, surprisingly, the ethercarboxylic acids obtained after a solvent-free carboxyalkylation, by directly distilling off the residual water present in the organic product phase under reduced pressure and subsequently filtering the metal salt precipitated (generally NaCl), have a low residual salt content of <0.20% which can be detected directly by conductivity measurements.

The invention therefore provides a process for preparing compounds of the formula (1)

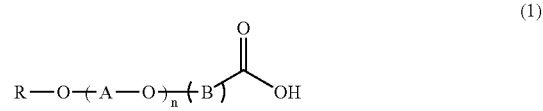

where

A is $C_2$- to $C_4$-alkylene,

B is $C_1$- to $C_4$-alkylene, n is a number from 1 to 100, and

R is $C_1$- to $C_{30}$-alkyl, $C_2$- to $C_{30}$-alkenyl, or $C_6$- to $C_{30}$-aryl, by alkylating a basic mixture of oxoalkylated alcohols of the formula

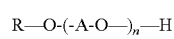

and alkoxides thereof with a $C_2$- to $C_5$-chlorocarboxylic acid in the absence of a solvent, converting the thus obtained ethercarboxylic acid salt to the free ethercarboxylic acid by adding an acid, the pH being adjusted to 3 or less, freeing the thus obtained ethercarboxylic acid, without washing, of water present down to a residual water content of <0.30% by distillation under reduced pressure, and removing the precipitated metal salts by filtration, so that the resulting product has a residual salt content of <0.2%.

The invention further provides the use of the compounds of the formula 1 and/or the salts thereof of the formula 2 prepared by this process

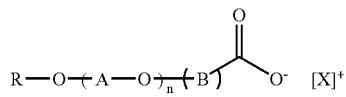

(2)

where A, n, B and R are each as defined above and X is a cation as metalworking assistants, in cosmetics formulations and as detergents in cleaning compositions. They are preferably used as metalworking assistants.

The invention further provides a process for preparing a cooling lubricant emulsion, wherein an ethercarboxylic acid is prepared by the process according to the invention and the thus obtained product is added to a cooling lubricant.

A is preferably propylene or ethylene, in particular ethylene. In a further preferred embodiment of the invention, the $-(A-O)_n-$ group is a mixed alkoxy group which may contain ethylene, propylene and butylene radicals. When it is a mixed alkoxy group, the ratio of the groups derived from ethylene oxide to the groups derived from propylene oxide or butylene oxide is preferably between 10:1 and 1:1.

n is preferably a number between 2 and 70, in particular from 3 to 50.

B is preferably a straight-chain alkylene group, in particular methylene. B may also be a branched alkylene group having 3 or 4 carbon atoms.

In a preferred embodiment, R is a $C_8-C_{24}$-, in particular a $C_{12}-C_{18}$-alkyl or -alkenyl radical. When R is an aromatic radical, preference is given to a phenyl radical having alkyl substitution between 4 and 12 carbon atoms.

In a preferred embodiment, X may be hydrogen ions. In a further preferred embodiment, X is alkali metal or alkaline earth metal ions, in particular lithium, sodium, potassium, magnesium or calcium.

In a further preferred embodiment, the cations used are ammonium ions of the formula $NR^1R^2R^3R^4$, where $R^1$, $R^2$, $R^3$ and $R^4$ are each independently H, $C_1$- to $C_{22}$-alkyl, $C_6$- to $C_{18}$-aryl, $C_7$- to $C_{22}$-alkylaryl and/or $C_1$- to $C_{22}$-alkenyl. The $R^1$, $R^2$, $R^3$ and $R^4$ radicals may contain heteroatoms such as N, P, O, S. The ammonium radicals may be monoalkylammonium, dialkylammonium, trialkylammonium or tetraalkylammonium radicals, in which case the alkyl substituents may each independently be occupied by up to 3 hydroxyl groups. X is preferably ammonium radicals which bear one, two, three or four $C_2$- to $C_{10}$-alkyl radicals. In a further preferred embodiment, one, two or three of the $R^1$ to $R^4$ radicals may be alkoxylated.

Suitable amines for the preparation of ammonium cations X are monoamines having primary or secondary amino function, such as methylamine, ethylamine, butylamine, laurylamine, coconut fatty amine, stearylamine, dimethylamine, diethylamine, dibutylamine, but also di- and polyamines, for example 3-dimethylaminopropylamine, 3-diethylaminopropylamine, 3-morpholinopropylamine, diethylenetriamine, triethylenetetramine or tetraethylenepentamine.

Suitable amino alcohols for the preparation of ammonium cations X are, for example, N,N-dimethylaminoethanol, N,N-diethylaminoethanol, N,N-dibutylaminoethanol, 3-dimethylaminopropanol, N-hydroxyethylmorpholine, monoethanolamine, diethanolamine, triethanolamine, 3-aminopropanol, isopropanolamine, 2-(2-aminoethoxy)ethanol and cyclohexylamino-N,N-diethanol.

Suitable base fatty alcohols for the process described here are linear or branched, saturated or unsaturated fatty alcohols having 1–30 carbon atoms, and also alkylphenols having a $C_1-C_{20}$-alkyl radical; preference is given to $C_6-C_{22}$ fatty alcohols.

According to the prior art, these may be reacted with alkylene oxides, for example ethylene oxide, propylene oxide, butylene oxide or mixtures of different such alkylene oxides, of which preference is given to ethylene oxide or mixtures of ethylene oxide and propylene oxide. Based on fatty alcohol, 1–100 mol of alkylene oxide are introduced, preferably 3–50 mol. The reaction temperatures are approx. 80–160° C.

In the subsequent reaction step, the alkoxide/alcohol oxyethylate mixture is reacted with a chlorocarboxylic acid derivative and a base, preferably dry sodium chloroacetate and sodium hydroxide. This may be effected by reacting the oxyethylate/alkoxide mixture with 100–150 mol % of sodium chloroacetate at 30–100° C. and simultaneously or successively admixing with solid sodium hydroxide or potassium hydroxide, so that the sum of the base present in the oxyethylate/alkoxide mixture and the amount of base additionally added corresponds to the amount of sodium chloroacetate.

After the carboxyalkylation, the alkali metal ethercarboxylate may be converted to the free ethercarboxylic acid by acidification to pH<3 with any acid. The aqueous phase is removed and the organic phase is freed directly, i.e. without using a washing process, of residual water present (approx. 5–15%) by distillation under reduced pressure. This precipitates the residual salt present which is subsequently removed in a filtration step. The thus obtained low-salt ethercarboxylic acid may subsequently be admixed again with an appropriate amount of deionized water in order to attain comparable physical properties analogous to the salt-containing, aqueous crude ethercarboxylic acid. In comparison to the crude ethercarboxylic acids which have a salt content of 0.60–1.50%, the ethercarboxylic acids prepared by the process described only have metal salts of <0.20%.

As the examples which follow show, ethercarboxylic acids having very low residual salt content of <0.20% can be prepared by the process disclosed here. Such ethercarboxylic acids generally have a conductivity of <15 μS/cm.

EXAMPLES

Example 1

Oleyl alcohol+10 EO-ECA (standard process=comparative example 1)

A 2 l stirred apparatus was initially charged with 412 g (0.57 mol) of oleyl alcohol+10 EO (e.g. Genapol O 100) under nitrogen flushing and heated to 40° C. With good stirring, 92.0 g (0.79 mol) of sodium chloroacetate were then introduced and the reaction mixture was heated to 50° C. Subsequently, a total of 35.0 g (0.88 mol) of sodium hydroxide microprills were added in portions in such a way that the internal temperature did not exceed 55° C. After each addition, the mixture was stirred for in each case 30 min, and at 70° C. for 2 h after the last addition. The reaction mixture was then heated to 90° C. and then warm hydrochloric acid (8–32%) was fed in until a pH of <3 had been attained. The reaction mixture was then mixed uniformly, heated to 100° C. and transferred to a heatable separation vessel with stirrer and bottom valve. Phase separation was effected without stirring at a temperature of approx. 100–110° C. After the aqueous lower phase had been removed, 448 g of product were obtained as a light yellow liquid.

Example 2

Oleyl alcohol+10 EO-ECA (removal of the residual water and filtration)

Oleyl alcohol+10 EO-ECA was prepared according to Example 1. After the aqueous lower phase had been removed, the residual water present (KF=8.9%) of the organic product phase was removed by distillation under a reduced pressure of 200–50 mbar and a temperature of 100° C. After the product phase had been cooled to 50–60° C., precipitated sodium chloride was removed by means of filtration. 395 g of low-salt product were obtained as a light yellow viscous liquid. To restore the physical properties, 8.9% deionized water was again subsequently mixed into the low-salt product.

Example 3 n-Octanol+8 EO (standard process=comparative example 2)

A 2 l stirred apparatus was initially charged with 362 g (0.75 mol) of n-octanol+8 EO (e.g. Genapol O 080) under nitrogen flushing and heated to 40° C. With good stirring, 104.8 g (0.90 mol) of sodium chloroacetate were then introduced and the reaction mixture was heated to 50° C. Subsequently, a total of 39.8 g (1.00 mol) of sodium hydroxide microprills were added in portions in such a way that the internal temperature did not exceed 55° C. After each addition, the mixture was stirred for in each case 30 min, and at 70° C. for 2 h after the last addition. The reaction mixture was then heated to 90° C. and then warm hydrochloric acid (35%) was fed in until a pH of <3 had been attained. The reaction mixture was then mixed uniformly, heated to 100° C. and transferred to a heatable separation vessel with stirrer and bottom valve. Phase separation was effected without stirring at a temperature of approx. 100–110° C. After the aqueous lower phase had been removed, 405 g of product were obtained as a light yellow liquid.

Example 4 n-Octanol+8 EO (removal of the residual water and filtration)

n-Octanol+8 EO-ECA was prepared according to Example 3. After the aqueous lower phase had been removed, the residual water present (KF=10.2%) of the organic product phase was removed by distillation under a reduced pressure of 200–50 mbar and a temperature of 100° C. After the product phase had been cooled to 50–60° C., precipitated sodium chloride was removed by means of filtration. 355 g of low-salt product were obtained as a light yellow viscous liquid. To restore the physical properties, 10.2% deionized water was again subsequently mixed into the low-salt product.

Example 5

Oleyl alcohol+10 EO-ECA
(standard process+washing with sodium chloride solution=comparative example 3)

A 2 l stirred apparatus was initially charged with 412 g (0.57 mol) of oleyl alcohol+10 EO (e.g. Genapol O 100) under nitrogen flushing and heated to 40° C. With good stirring, 92.0 g (0.79 mol) of sodium chloroacetate were then introduced and the reaction mixture was heated to 50° C. Subsequently, a total of 35.0 g (0.88 mol) of sodium hydroxide microprills were added in portions in such a way that the internal temperature did not exceed 55° C. After each addition, the mixture was stirred for in each case 30 min, and at 70° C. for 2 h after the last addition. The reaction mixture was then heated to 90° C. and then warm hydrochloric acid (8–32%) was fed in until a pH of <3 had been attained. The reaction mixture was then mixed uniformly, heated to 100° C. and transferred to a heatable separation vessel with stirrer and bottom valve. Phase separation was effected without stirring at a temperature of approx. 100–110° C. After the aqueous lower phase had been removed the crude product was washed twice with a saturated aqueous sodium chloride solution. After the washing phase had been removed, 439 g of product were obtained as a light yellow liquid.

TABLE 1

Characteristic parameters of the ethercarboxylic acids

| Example | NaCl content [%] | Conductivity [μS/cm] | Conductivity [μS/cm] (0.05 M in water) | AN [mg KOH/g] | HN [mg KOH/g] |
|---|---|---|---|---|---|
| 1 (C) | 0.87 | 47.0 | 1182 | 72.2 | 73.6 |
| 2 | 0.09 | 4.93 | 726 | 71.9 | 73.8 |
| 3 (C) | 0.95 | 93.2 | 2480 | 105.2 | 107.5 |
| 4 | 0.12 | 11.4 | 1362 | 104.9 | 107.4 |
| 5 (C) | 0.78 | 46.8 | 1175 | 72.1 | 73.6 |

(AN = acid number, HN = hydrolysis number)

As is evident from Table 1, the ethercarboxylic acids prepared by the process disclosed here feature a particularly low salt content (sodium chloride), which manifests itself by a distinctly lower conductivity in comparison to the ethercarboxylic acids from the standard process. In addition, the comparison of the acid and hydrolysis numbers found shows that the process described hardly results in any increased (undesired) ester formation. Although a prior art washing process can slightly lower the sodium chloride content of ethercarboxylic acids (see comparative example 3), salt contents of below 0.2% are not achievable in this way.

Use of the inventive compounds as corrosion inhibitors for water-miscible cooling lubricants, cleaning liquids and for surface treatments.

The corrosion protection was tested based on the DIN standard 51360, Part 2 (filter paper test) and served to assess the corrosion of iron metal. The measure of the corrosion used is the type and number of corrosion marks on a round filter paper which result from the action of a cooling lubricant (CL) mixed with water on standardized gray iron turnings (turning size: from 3 to 6 mm$^2$). The assessment was by visual testing and grading of the degree of corrosion (1 to 4) according to a comparison table.

For the investigations of corrosion protection, the products to be tested were adjusted to pH 9.0 with triethanolamine (TEA) to form the corresponding ammonium salt.

TABLE 2

Testing of corrosion protection according to DIN (filter paper test), data in degrees of corrosion 1 to 4 according to comparison table, DIN standard 51360, Part 2 (filter paper test), concentrations in % by weight

| ECA from Example | NaCl content [%] | Concentration of the ethercarboxylic acid (ECA) | | |
|---|---|---|---|---|
| | | 3% | 4% | 5% |
| 1 (C) | 0.87 | 4 | 3–4 | 3 |
| 2 | 0.09 | 2 | 1–2 | 1 |
| 3 (C) | 0.95 | 3–4 | 3–4 | 3 |
| 4 | 0.12 | 2–3 | 1–2 | 1 |
| 5 (C) | 0.78 | 4 | 3–4 | 3 |

As is evident from Table 2, the low salt content of the ethercarboxylic acids leads to a distinctly improved corrosion protection performance of the inventive ethercarboxylic acids.

What is claimed is:

1. A process for preparing compounds of the formula (1)

$$R-O-(A-O)_n-(B)-C(=O)-OH \quad (1)$$

where
  A is $C_2$- to $C_4$-alkylene,
  B is $C_1$- to $C_4$-alkylene,
  n is a number from 1 to 100, and
  R is $C_1$- to $C_{30}$-alkyl, $C_2$- to $C_{30}$-alkenyl, or $C_6$- to $C_{30}$-aryl, by
  a) alkylating a basic mixture of oxoalkylated alcohols of the formula $$R-O-(-A-O-)_n-H$$

and alkoxides thereof with a $C_2$- to $C_5$-chlorocarboxylic acid in the absence of a solvent,
  b) converting the thus obtained ethercarboxylic acid salt to the free ethercarboxylic acid by adding an acid, the pH being adjusted to 3 or less,
  c) freeing the thus obtained ethercarboxylic acid, without washing, of water present down to a residual water content of <0.30% by distillation under reduced pressure, and
  d) removing the precipitated metal salts by filtration, so that the resulting product has a residual salt content of <0.2%.

2. The process as claimed in claim 1, wherein A is propylene or ethylene.

3. The process as claimed in claim 1, wherein n is a number between 2 and 70.

4. The process of claim 1, wherein B is a methylene group.

5. The process of claim 1, wherein R is a $C_8$- to $C_{24}$-alkyl or -alkenyl radical.

6. The process of claim 1, wherein the acid of step(b) is hydrochloric acid or sulfuric acid.

7. A process for preparing a cooling lubricant emulsion, said process comprising adding to the cooling lubricant emulsion an ethercarboxylic acid of formula (1)

$$R-O-(A-O)_n-(B)-C(=O)-OH \quad (1)$$

where
  A is $C_2$- to $C_4$-alkylene,
  B is $C_1$- to $C_4$-alkylene,
  n is a number from 1 to 100, and
  R is $C_1$- to $C_{30}$-alkyl, $C_2$- to $C_{30}$-alkenyl, or $C_8$- to $C_{30}$-aryl,
  prepared by the process of claim 1.

8. A method for inhibiting corrosion of iron metal, said method comprising contacting the iron metal with the compounds of the formula 1

$$R-O-(A-O)_n-(B)-C(=O)-OH \quad (1)$$

where
  A is $C_2$- to $C_4$-alkylene,
  B is $C_1$- to $C_4$-alkylene,
  n is a number from 1 to 100, and
  R is $C_1$- to $C_{30}$-alkyl, $C_2$- to $C_{30}$-alkenyl, $C_6$- to $C_{30}$-aryl,
  or the salts thereof or mixtures of the compounds of formula (1) and the salts thereof of the formula 2 prepared by the process of claim 1

$$R-O-(A-O)_n-(B)-C(=O)-O^- \; [X]^+ \quad (2)$$

where X is a cation.

9. A method for cleaning a surface, said method comprising contacting the surface with a cleaning composition comprising the compounds of formula (1)

$$R-O-(A-O)_n-(B)-C(=O)-OH \quad (1)$$

where
  A is $C_2$- to $C_4$-alkylene,
  B is $C_1$- to $C_4$-alkylene,
  n is a number from 1 to 100, and
  R is $C_1$- to $C_{30}$-alkyl, $C_2$- to $C_{30}$-alkenyl, or $C_8$- to $C_{30}$-aryl,
  or a salt or mixtures of the compound of formula (1) and the salt according to formula (2)

(2)

wherein X is a cation selected from the group consisting of an alkali metal ion, an alkaline earth metal ion, an ammonium ion, and mixtures thereof, wherein the compound of formula (1) is prepared by the process of claim 1.

10. A method for cleaning a surface, said method comprising contacting the surface with a cleaning composition comprising the compounds of formula (1)

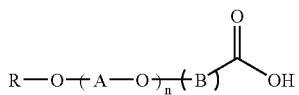
(1)

where
A is $C_2$- to $C_4$-alkylene,
B is $C_1$- to $C_4$-alkylene,
n is a number from 1 to 100, and
R is $C_1$- to $C_{30}$-alkyl, $C_2$- to $C_{30}$-alkenyl, or $C_8$- to $C_{30}$-aryl, or a salt mixtures of the compound of formula (1) and the salt according to formula (2)

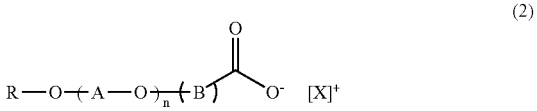
(2)

wherein X is a cation selected from the group consisting of an alkali metal ion, an alkaline earth metal ion, an ammonium ion, and mixtures thereof, wherein the compound of formula (1) is prepared by the process of claim 1.

* * * * *